(12) United States Patent
Murata et al.

(10) Patent No.: US 7,566,801 B2
(45) Date of Patent: Jul. 28, 2009

(54) POLYFLUOROALKYL ALCOHOL, OR (METH)ACRYLIC ACID DERIVATIVE THEREOF, AND PROCESS FOR PRODUCING THE SAME

(75) Inventors: Seiichiro Murata, Ibaraki (JP); Masayosi Horiuti, Ibaraki (JP); Katsuyuki Sato, Ibaraki (JP); Hideki Abe, Ibaraki (JP); Haruyoshi Tatsu, Ibaraki (JP)

(73) Assignee: Unimatec Co., Ltd, Tokyo (JP)

( * ) Notice: Subject to any disclaimer, the term of this patent is extended or adjusted under 35 U.S.C. 154(b) by 0 days.

(21) Appl. No.: 12/224,969

(22) PCT Filed: Mar. 9, 2007

(86) PCT No.: PCT/JP2007/054678

§ 371 (c)(1),
(2), (4) Date: Sep. 10, 2008

(87) PCT Pub. No.: WO2007/105633

PCT Pub. Date: Sep. 20, 2007

(65) Prior Publication Data

US 2009/0036706 A1   Feb. 5, 2009

(30) Foreign Application Priority Data

Mar. 10, 2006   (JP) .............................. 2006-065188

(51) Int. Cl.
*C07C 67/36* (2006.01)

(52) U.S. Cl. ........................................ 560/232; 568/842
(58) Field of Classification Search ........................ None
See application file for complete search history.

(56) References Cited

U.S. PATENT DOCUMENTS 3,916,009 A    10/1975   Jager
3,919,183 A  * 11/1975   Jager et al. .................. 526/245

FOREIGN PATENT DOCUMENTS

DE         23 46 289       3/1975
JP         59-108081       6/1984
WO         WO 95/11877     5/1995

* cited by examiner

*Primary Examiner*—Karl J Puttlitz
(74) *Attorney, Agent, or Firm*—Butzel Long

(57) ABSTRACT

A polyfluoroalkyl alcohol, or a (meth)acrylic acid derivative thereof, represented by the following general formula:

$$C_nF_{2n+1}(CH_2CF_2)_a(CF_2CF_2)_b(CH_2CH_2)_cOR$$

(R:H or (meth)acrylic acid group; n: 1-6; a: 1-4; b: 1-3; and c: 1-3). Polyfluoroalkyl alcohol (R: hydrogen atom) can be produced by reaction of fluoroalkyl iodide represented by the following general formula:

$$C_nF_{2n+1}(CH_2CF_2)_a(CF_2CF_2)_b(CH_2CH_2)_cI$$

with N-methyl formamide, followed by hydrolysis in the presence of an acid catalyst, whereas polyfluoroalkyl alcohol (meth)acrylic acid derivative (R: (meth)acrylic acid group) can be produced by reaction of the polyfluoroalkyl alcohol with (meth)acrylic acid.

5 Claims, No Drawings

POLYFLUOROALKYL ALCOHOL, OR (METH)ACRYLIC ACID DERIVATIVE THEREOF, AND PROCESS FOR PRODUCING THE SAME

TECHNICAL FIELD

The present invention relates to a polyfluoroalkyl alcohol, or a (meth)acrylic acid derivative thereof, and a process for producing the same, and more particularly to a polyfluoroalkyl alcohol or a (meth)acrylic acid derivative thereof for effective use as a surfactant, a raw material monomer for a water- and oil-repellent, etc., and a process for producing the same.

BACKGROUND ART

Acrylic acid derivatives of polyperfluoroalkyl alcohol, for example, $CF_3(CF_2)_7CH_2CH_2OCOCH=CH_2$ are used in a large amount as a monomer for synthesis of a water- and oil-repellent for fibers. Perfluoroalkyl alcohol as an acrylation precursor is widely used as a surfactant, etc.

Patent Literature 1: JP-B-63-22237

According to recent reports, the compounds having a perfluoroalkyl group of more or less 8 carbon atoms have a high degree of biological accumulation, and have an environmental problem among the acrylate derivatives, with the result of fear of serious future problems in their production and use. However, the compounds having a perfluoroalkyl group of not more than 6 carbon atoms are said to have a low degree of biological accumulation.

DISCLOSURE OF THE INVENTION

Problem to be Solved by the Invention

An object of the present invention is to provide a polyfluoroalkyl alcohol, or a (meth)acrylic acid derivative thereof, having a perfluoroalkyl group of not more than 6 carbon atoms, which is said to have a low degree of biological accumulation, and can be effectively used as a surfactant or a raw material monomer for a water- and oil-repellent, etc., and a process for producing the same.

Means for Solving the Problem

The present invention provides a polyfluoroalkyl alcohol, or a (meth)acrylic acid derivative thereof, represented by the following general formula:

$$C_nF_{2n+1}(CH_2CF_2)_a(CF_2CF_2)_b(CH_2CH_2)_cOR \qquad [I]$$

(where R is a hydrogen atom, an acrylic acid group, or a methacrylic acid group, n is an integer of 1 to 6, a an integer of 1 to 4, b an integer of 1 to 3, and c an integer of 1 to 3, the adjacent group to the $C_nF_{2n+1}$ group being a $CH_2CF_2$ group).

Polyfluoroalkyl alcohol (R: a hydrogen atom) [Ia] can be prepared by reaction of a polyfluoroalkyl iodide represented by the following general formula with N-methyl formamide, followed by hydrolysis in the presence of an acid catalyst:

$$C_nF_{2n+1}(CH_2CF_2)_a(CF_2CF_2)_b(CH_2CH_2)_cI \qquad [II]$$

(Meth)acrylic acid derivative of polyfluoroalkyl alcohol (R: an acrylic acid group or a methacrylic acid group) [Ib] can be prepared by esterification reaction of the polyfluoroalkyl alcohol [Ia] with acrylic acid or methacrylic acid.

EFFECT OF THE INVENTION

The present polyfluoroalkyl alcohol or (meth)acrylic acid derivative thereof is not only made of a perfluoroalkyl group of not more than 6 carbon atoms, which has a low degree of biological accumulation, but also has a $CH_2CF_2$ group derived from vinylidene fluoride in the molecule, the $CH_2CF_2$ group being readily dehydrofluorination to form double bond and readily susceptible to ozone decomposition, giving less environmental hazard. The present polyfluoroalkyl alcohol can be effectively used as a surfactant, and the present (meth)acrylic acid derivative thereof can be also effectively used as monomers for synthesis of water- and oil-repellents in the same manner as the conventional compounds.

BEST MODES FOR CARRYING OUT THE INVENTION

Polyfluoroalkyl iodide [II] as a starting material for synthesis of polyfluoroalkyl alcohol [Ia] can be prepared by addition reaction of ethylene to a terminally iodized compound represented by the following general formula:

$$C_nF_{2n+1}(CH_2CF_2)_a(CF_2CF_2)_bI \qquad [III]$$

The addition reaction of ethylene can be carried out by adding pressurized ethylene to the above-mentioned compound [III] in the presence of a peroxide initiator, where the number of added ethylene is 1-3, preferably 1, though dependent on reaction conditions. Though the reaction temperature depends on decomposition temperature of the initiator used, the reaction is usually carried out at about 80° to about 120° C., and can be carried out at 80° C. or lower, when a peroxide initiator decomposable at low temperatures is used.

The peroxide initiator for use in the present invention includes, for example, t-butyl peroxide, di(t-butylcyclohexyl) peroxydicarbonate, dicetyl peroxydicarbonate, di-n-propyl peroxycarbonate, diisopropyl peroxycarbonate, di-sec-butyl peroxycarbonate, etc., and can be used in a proportion of about 1 to about 5% by mole on the basis of the compound [III] from the viewpoint of reaction rate and controllability.

The afore-mentioned terminally iodized compound [III] can be synthesized through a series of the following steps:

(1) Perfluoroalkyl iodide represented by the following general formula:

$$C_nF_{2n+1}I \ (n: 1 \text{ to } 6)$$

is allowed to react with vinylidene fluoride in the presence of the aforementioned peroxide initiator (in a proportion of about 0.1 to about 0.5% by mole on the basis of the raw material compounds) to obtain a compound represented by the following general formula:

$$C_nF_{2n+1}(CH_2CF_2)_aI \qquad [IV]$$

(2) The compound represented by the above-mentioned general formula [IV] is allowed to react with tetrafluoroethylene in the presence of a peroxide initiator to obtain a terminally iodized compound represented by the above-mentioned general formula [III]. In the general formula [III], b is an integer of 1 to 3, preferably 1 or 2. The peroxide initiator for use in the reaction is the same organic peroxide initiator as mentioned above in the same proportion as in (1).

Reaction temperature of vinylidene fluoride or tetrafluoroethylene addition reaction depends on the decomposition temperature of an initiator used, but the reaction can be carried out at 80° C. or lower even under low pressure conditions by using a peroxide initiator decomposable at low temperatures. The reaction can be carried out by charging $C_nF_{2n+1}I$ or the above-mentioned compound [IV] into an autoclave, elevating the inside temperature to about 10° to about 60° C., for example, 50° C., then adding a peroxide initiator dissolved in $C_nF_{2n+1}I$ or the compound [IV] thereto, and, when the inside temperature reaches, for example, to 55° C., adding vinylidene fluoride or tetrafluoroethylene portion-wise thereto, while keeping the pressure at about 0.1 to about 10 MPa, and after the portion-wise addition of the desired amount, conducting aging at about 55° to about 80° C. for about one hour. Integer a or b of vinylidene fluoride or tetrafluoroethylene skeleton as added by the reaction depends on the amount of the portion-wise added vinylidene fluoride or tetrafluoroethylene. Generally, mixtures having various integers a and b are formed.

Reactions at low temperatures can not only reduce the energy consumption, but also suppress corrosion of apparatuses due to hydrofluoric acid, etc., and also reduce the frequency of apparatus renewal. Furthermore, less expensive materials can be used thereby, and thus together with the reduction in the renewal frequency, the capital investment can be suppressed to a lower cost.

The specific compounds [III] subject to the ethylene addition includes, for example, the following compounds. The compounds are in a mixture of oligomers having various integers a and b, and oligomers having specific integers a and b can be isolated one from another by distillation. Oligomers failing to satisfy the specific integers a and b can be reused again in number-increasing reaction of oligomers with vinylidene fluoride or tetrafluoroethylene after isolation or as such in mixtures:

$C_2F_5(CH_2CF_2)(CF_2CF_2)I$ $C_2F_5(CH_2CF_2)(CF_2CF_2)_2I$ $C_2F_5(CH_2CF_2)_2(CF_2CF_2)I$ $C_2F_5(CH_2CF_2)_2(CF_2CF_2)_2I$ $C_4F_9(CH_2CF_2)(CF_2CF_2)I$ $C_4F_9(CH_2CF_2)_2(CF_2CF_2)I$ $C_4F_9(CH_2CF_2)(CF_2CF_2)_2I$ $C_4F_9(CH_2CF_2)_2(CF_2CF_2)_2I$

Polyfluoroalkyl alcohol [Ia], one of the desired compounds of the present invention, can be prepared by allowing polyfluoroalkyl iodide [II] to react with N-methyl formamide $HCONH(CH_3)$ at first to form a mixture of polyfluoroalkyl alcohol with its formic acid ester, and then subjecting the mixture to hydrolysis reaction in the presence of an acid catalyst. In the general formula [Ia], c is an integer of 1 to 3, preferably 1 or 2. To prevent the yield from lowering due to dehydrofluorination of $CH_2CF_2$ derived from vinylidene fluoride combined into polyfluoroalkyl iodide, it is preferable to use an about 5- to about 10-fold amount by mole of N-methyl formamide, and an aqueous solution of p-toluenesulfonic acid as an acid catalyst. Reaction with N-methyl formamide is carried out at about 140° to about 160° C. for about 4 to about 5 hours, and the successive hydrolysis reaction at about 70° to about 90° C. for about 7 to about 8 hours.

The resulting polyfluoroalkyl alcohol [Ia] can be formed into a (meth)acrylic acid derivative [Ib] by esterification reaction thereof with acrylic acid or methacrylic acid. Esterification reaction can be carried out by adding an aromatic hydrocarbon solvent such as toluene, benzene, etc., a catalyst such as p-toluenesulfonic acid, etc., and a polymerization inhibitor such as hydroquinone to polyfluoroalkyl alcohol, heating the mixture at about 90° to about 100° C., then adding an about 1- to about 2-fold amount by mole of acrylic acid or methacrylic acid thereto, and heating the mixture at about 110° to about 120° C. for about 2 to about 5 hours to conduct dehydration and esterification.

EXAMPLES

The present invention will be described in detail below, referring to Examples.

Reference Example 1

500 g of perfluorobutyl iodide $C_4F_9I$ (purity: 82.9%) was charged into an autoclave having a capacity of 1,200 ml. When the inside temperature reached to 50° C. by heating, 0.75 g of a di(4-t-butylcyclohexyl) peroxydicarbonate initiator (Percadox 16, a product of Kayaku-Aquzo Co., Ltd.) dissolved in 60 g of $C_4F_9I$ was added thereto. When the inside temperature reached to 55° C., vinylidene fluoride was portion-wise added thereto, while keeping the pressure at 0.5-0.7 MPa, and when the portion-wise added amount reached to 214 g, aging was conducted at 55°-65° C. for one hour to complete the reaction. Then, the reaction mixture was cooled to recover 583 g of the product.

The resulting product was subjected to separation by distillation under conditions of column top temperature: 58° C. and pressure: 7.4 kPa (56 mmHg) to obtain 203 g of $CF_3(CF_2)_3(CH_2CF_2)I$ (purity: 99.5%), which was used as a raw material in Reference Examples 2 and 3. At the same time the reaction product $CF_3(CF_2)_3(CH_2CF_2)_2I$ was separated by distillation under conditions of column top temperature: 74° C. and pressure: 2.6 kPa (20 mmHg).

Reference Example 2

600 g of $CF_3(CF_2)_3(CH_2CF_2)I$ (purity: 99.5%) was charged into an autoclave having a capacity of 1,200 ml, and when the inside temperature reached to 50° C. by heating, 1.35 g of a peroxide initiator (Percadox 16) dissolved in 300 g of $CF_3(CF_2)_3(CH_2CF_2)I$ was added thereto. When the inside temperature reached to 55° C., tetrafluoroethylene was portion-wise added thereto, while keeping the pressure at 0.2-0.3MPa, and when the portion-wise added amount reached to 150 g, aging was conducted at 55°-74° C. for one hour to complete the reaction. Then, the reaction mixture was cooled to recover 1,010 g of the product.

The resulting product was subjected to separation by distillation under conditions of column top temperature: 71° C. and pressure: 2.6 kPa (20 mmHg) to obtain 347 g of $CF_3(CF_2)_3(CH_2CF_2)(CF_2CF_2)I$ (purity: 99.8%), which was used as a raw material in Reference Example 3.

Reference Example 3

830 g of a mixture of $CF_3(CF_2)_3(CH_2CF_2)I$ (purity: 99.5%) and $CF_3(CF_2)_3(CH_2CF_2)(CF_2CF_2)I$ (purity: 99.8%) in a ratio of 35.4:64.0 by weight was charged into an autoclave having a capacity of 1,200 ml, and when the inside temperature reached to 50° C. by heating, 1.68 g of a peroxide initiator (Percadox 16) dissolved in 300 g of the mixture having the afore-mentioned mixing ratio was added thereto. When the inside temperature reached to 55° C., tetrafluoroethylene was portion-wise added thereto, while keeping the pressure at 0.2-0.3 MPa. When the portion-wise added amount reached to 150 g, aging was conducted at 55°-78° C. for one hour to complete the reaction. Then, the reaction mixture was cooled to recover 1,257 g of the product mixture.

The resulting product mixture was subjected to separation by distillation to obtain 184 g of $CF_3(CF_2)_3(CH_2CF_2)I$ (purity: 99.7%), 575 g of $CF_3(CF_2)_3(CH_2CF_2)(CF_2CF_2)I$ (purity: 99.4%), and 302 g of $CF_3(CF_2)_3(CH_2CF_2)(CF_2CF_2)_2I$ (purity: 99.3%). Separation of $CF_3(CF_2)_3(CH_2CF_2)I$ and $CF_3(CF_2)_3(CH_2CF_2)(CF_2CF_2)I$ by distillation was carried out under the same distillation conditions as above-mentioned, whereas that of $CF_3(CF_2)_3(CH_2CF_2)(CF_2CF_2)_2I$ was carried out under distillation conditions of column top temperature: 91° C. and pressure: 0.8 kPa (6.0 mmHg).

Analytical results by gas chromatography (GC) of products obtained in the foregoing Reference Examples are given in the following Table in terms of GC % of compounds represented by the following general formula having various integers of n, a, and b:

$$C_nF_{2n+1}(CH_2CF_2)_a(CF_2CF_2)_bI$$

TABLE

|   |   |   | Ref. Ex. 1 | | Ref. Ex. 2 | | Ref. Ex. 3 | |
|---|---|---|---|---|---|---|---|---|
| n | a | b | Raw material | Product | Raw material | Product | Raw material | Product |
| 4 | 0 | 0 | 82.9 | 5.6 | | | | |
| 4 | 1 | 0 | | 61.4 | 99.5 | 44.7 | 35.4 | 14.8 |
| 4 | 2 | 0 | | 20.2 | | | | |
| 4 | 3 | 0 | | 2.4 | | | | |
| 4 | 4 | 0 | | 0.2 | | | | |
| 4 | 1 | 1 | | | | 37.1 | 64.0 | 46.2 |
| 4 | 1 | 2 | | | | 12.0 | | 23.9 |
| 4 | 1 | 3 | | | | 3.5 | | 9.3 |
| 4 | 1 | 4 | | | | 0.8 | | 3.0 |
| 4 | 1 | 5 | | | | 0.2 | | 0.8 |
| 4 | 1 | 6 | | | | | | 0.2 |
| $C_6F_{13}H$ | | | 16.7 | 7.9 | | | | |

Remark)
$C_6F_{13}H(CF_3CF_2CF_2CF_2CF_2CF_2H)$ is an impurity contained in the raw material $C_4F_9I$, and has a boiling point very close to that of $C_4F_9I$, and thus is a hardly separable substance, but it does not take part in the reaction and thus can be used as such without any isolation in the successive reaction.

Example 1

(1) 603 g (1.17 moles) of $CF_3(CF_2)_3(CH_2CF_2)(CF_2CF_2)I$ (99.8 GC %) and 7 g (3.85 mol. %) of di-t-butyl peroxide were charged into an autoclave having a capacity of 1,200 ml, provided with a stirrer and a thermometer, and then the autoclave was deaerated by a vacuum pump. When the inside temperature reached to 80° C. by heating, ethylene was consecutively added thereto to keep the inside pressure at 0.5 MPa. When the inside pressure was lowered to 0.2 MPa, ethylene was again added thereto to keep the inside pressure at 0.5 MPa and such an operation was repeated. 49 g (1.7 moles) of ethylene was added thereto over about 3 hours, while keeping the inside temperature at 80°-115° C. The autoclave contents were recovered at inside temperatures of 50° C. or lower to obtain 635 g (yield: 98.8%) of $CF_3(CF_2)_3(CH_2CF_2)(CF_2CF_2)(CH_2CH_2)I$ (98.3 GC %).

(2) 100 g (0.18 moles) of $CF_3(CF_2)_3(CH_2CF_2)(CF_2CF_2)(CH_2CH_2)I$ (98.3 GC %) obtained in the above (1) and 100 g (1.68 moles) of N-methyl formamide were charged into a three-necked flask having a capacity of 200 ml, provided with a condenser and a thermometer, and stirred at 150° C. for 4 hours. After completion of the reaction, the reaction mixture was washed with 30 ml of water, and the resulting lower layer (82.8 g) was mixed with 83 g of an aqueous 15 wt. % p-toluenesulfonic acid solution, and stirred at 80° C. for 8 hours. The reaction mixture was allowed to stand to obtain 60 g (yield: 62.6%) of a reaction product (78.4 GC %) in the form of a transparent, colorless liquid at the ordinary temperature, as a lower layer.

The reaction product was subjected to subatmospheric distillation under conditions of inside pressure: 0.2 kPa, inside temperature: 100°-144° C., and column top temperature: 58°-59° C., to obtain 43.7 g (distillation yield: 88.2%) of purified reaction product (95.4 GC %).

It was found from the results of $^1$H-NMR and $^{19}$F-NMR that the resulting purified reaction product was compound represented by the following formula:

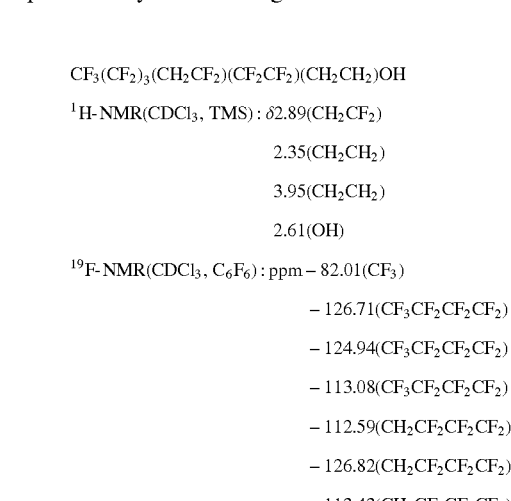

Example 2

(1) 529 g (0.86 moles) of $CF_3(CF_2)_3(CH_2CF_2)(CF_2CF_2)_2I$ (99.9 GC %) obtained in Reference Example 3, and 5 g (3.76 mol. %) of di-t-butyl peroxide were used and reaction introducing 34 g (1.2 moles) of ethylene thereto were carried out in the same manner as in Example 1 (1) to obtain 550 g (yield: 99.4%) of $CF_3(CF_2)_3(CH_2CF_2)(CF_2CF_2)_2(CH_2CH_2)I$ (99.1 GC %).

(2) 150 g (0.24 moles) of $CF_3(CF_2)_3(CH_2CF_2)(CF_2CF_2)_2(CH_2CH_2)I$ (99.1 GC %) obtained in the above (1) and 105 g (1.78 moles) of N-methyl formamide were charged into a three-necked flask having a capacity of 200 ml, provided with a condenser and a thermometer, and stirred at 150° C. for 5 hours. After completion of the reaction, the reaction mixture was washed with 40 ml of water, and the resulting lower layer (132.3 g) was mixed with 135 g of an aqueous 15 wt. % p-toluenesulfonic acid solution, and stirred at 80° C. for 7 hours. The reaction mixture was allowed to stand to obtain 103 g (yield: 53.5%) of reaction product (65.5 GC %) in the form of white solid matters at the ordinary temperature, as a lower layer.

The reaction product was subjected to subatmospheric distillation under conditions of inside pressure: 0.2 kPa, inside temperature: 121°-163° C., and column top temperature: 760-77° C. to obtain 66.9 g (distillation yield: 94.2%) of purified reaction product (95.3 GC %).

It was found from the results of $^1$H-NMR and $^{19}$F-NMR that the resulting purified reaction product was a compound represented by the following formula:

$CF_3(CF_2)_3(CH_2CF_2)(CF_2CF_2)_2(CH_2CH_2)OH$ $^1H\text{-NMR}(CDCl_3, TMS): \delta 2.91(CH_2CF_2)$ 2.39($CH_2CH_2$)

3.99($CH_2CH_2$)

1.83(OH)

$^{19}F\text{-NMR}(CDCl_3, C_6F_6): ppm - 82.11(CF_3)$

−126.92($CF_3CF_2CF_2CF_2$)

−125.11($CF_3CF_2CF_2CF_2$)

−113.11, −113.17

($CF_2CH_2CF_2$)

−122.43($CH_2CF_2CF_2CF_2$)

−124.49($CH_2CF_2CF_2CF_2$)

−114.52($CF_2CF_2CH_2CH_2$)

−124.94($CF_2CF_2CH_2CH_2$)

Example 3

40.0 g (0.09 moles) of the reaction product (95.4 GC %) obtained in Example 1, 21 g of toluene, 1.7 g of p-toluenesulfonic acid, and 0.05 g of hydroquinone were charged into a three-necked flask having a capacity of 100 ml, provided with a condenser and a thermometer, heated to an inside temperature of 100° C., then admixed with 10.2 g (0.14 moles) of acrylic acid, and stirred at an inside temperature of 115° C. for 2 hours. After completion of the reaction, 72 g of a reaction product solution was recovered by cooling, followed by removal of toluene therefrom by an evaporator, 44.5 g of the residues were washed with city water to obtain 40.9 g (yield: 82.6%) of reaction product (86.3 GC %) in the form of a transparent, colorless liquid at the ordinary temperature, as a lower layer.

The reaction product was subjected to subatmospheric distillation under conditions of inside pressure: 0.2 kPa, inside temperature: 103°-143° C., and column top temperature: 60°-61° C. to obtain 15.7 g (distillation yield: 44%) of purified reaction product (99.4 GC %).

It was found from the results of $^1$H-NMR and $^{19}$F-NMR that the resulting purified reaction product was a compound represented by the following formula:

$CF_3(CF_2)_3(CH_2CF_2)(CF_2CF_2)(CH_2CH_2)OCOCH=CH_2$ $^1H\text{-NMR}(CDCl_3, TMS): \delta 2.91(CH_2CF_2)$ 2.52($CH_2CH_2$)

4.46($CH_2CH_2$)

6.13(CH=$CH_2$)

6.41, 5.88(CH=$CH_2$)

$^{19}F\text{-NMR}(CDCl_3, C_6F_6): ppm - 81.98(CF_3)$

−126.71($CF_3CF_2CF_2CF_2$)

−124.93($CF_3CF_2CF_2CF_2$)

−113.00($CF_3CF_2CF_2CF_2$)

-continued

−112.56($CH_2CF_2CF_2CF_2$)

−126.71($CH_2CF_2CF_2CF_2$)

−113.57($CH_2CF_2CF_2CF_2$)

Example 4

60.0 g (0.11 mole) of the reaction product obtained in Example 2, 29 g of toluene, 1.6 g of p-toluenesulfonic acid, and 0.07 g of hydroquinone were charged into a three-necked flask having a capacity of 100 ml, provided with a condenser and a thermometer, heated to an inside temperature of 100° C., then admixed with 10 g (0.14 moles) of acrylic acid, and stirred at an inside temperature of 118° C. for 3 hours. After completion of the reaction, 82 g of a reaction product solution was recovered by cooling, followed by removal of toluene therefrom by an evaporator, 63.9 g of the residues were washed with city water to obtain 60.8 g (yield: 86.4%) of reaction product (89.3 GC %), in the form of a transparent, colorless liquid at the ordinary temperature, as a lower layer.

The resulting reaction product was subjected to subatmospheric distillation under conditions of inside pressure: 0.2 kPa, inside temperature: 125°-155° C., and column top temperature: 84°-86° C. to obtain 42.2 g (distillation yield: 77%) of purified reaction product (99.4 GC %).

It was found from the results of $^1$H-NMR and $^{19}$F-NMR that the resulting purified reaction product was a compound represented by the following formula:

$CF_3(CF_2)_3(CH_2CF_2)(CF_2CF_2)_2(CH_2CH_2)OCOCH=CH_2$ $^1H\text{-NMR}(CDCl_3, TMS): \delta 2.91(CH_2CF_2)$ 2.51($CH_2CH_2$)

4.46($CH_2CH_2$)

6.13(CH=$CH_2$)

6.41, 5.88(CH=$CH_2$)

$^{19}F\text{-NMR}(CDCl_3, C_6F_6): ppm - 81.95(CF_3)$

−126.64($CF_3CF_2CF_2CF_2$)

−124.80($CF_3CF_2CF_2CF_2$)

−112.83($CF_2CH_2CF_2$)

−122.05($CH_2CF_2CF_2CF_2$)

−124.13($CH_2CF_2CF_2CF_2$)

−114.36($CF_2CF_2CH_2CH_2$)

−124.45($CF_2CF_2CH_2CH_2$)

The invention claimed is:

1. A polyfluoroalkyl alcohol, or a (meth)acrylic acid derivative thereof, represented by the following general formula:

$$C_nF_{2n+1}(CH_2CF_2)_a(CF_2CF_2)_b(CH_2CH_2)_cOR \quad [I]$$

(where R is a hydrogen atom, an acrylic acid group, or a methacrylic acid group ; n is an integer of 1 to 6 ; a an integer of 1 to 4 ; b an integer of 1 to 3, and c and integer of 1 to 3, the adjacent group to the $C_nF_{2n+1}$ group being a $CH_2CF_2$ group).

2. A process for producing a polyfluoroalkyl alcohol, represented by the following general formula:

$$C_nF_{2n+1}(CH_2CF_2)_a(CF_2CF_2)_b(CH_2CH_2)_cOH \quad [Ia]$$

(where n is an integer of 1 to 6 ; a an integer of 1 to 4, b an integer of 1 to 3, and c an integer of 1 to 3, the adjacent group to the $C_nF_{2n+1}$ group being a $CH_2CF_2$ group), which process comprises allowing a polyfluoroalkyl iodide, represented by the following general formula:

$$C_nF_{2n+1}(CH_2CF_2)_a(CF_2CF_2)_b(CH_2CH_2)_cI \quad [II]$$

(where n, a, b and c have the same meanings as defined above) to react with N-methyl formamide, followed by hydrolysis reaction in the presence of an acid catalyst.

3. A process for producing a polyfluroalkyl alcohol according to claim 2, wherein a 5- to 10-fold amount by mole of the N-methylformamide is used on the basis of the polyfluoroalkyl iodide.

4. A process for producing a polyfluroalkyl alcohol according to claim 2, wherein the acid catalyst is p-toluenesulfonic acid.

5. A process for producing a polyfluroalkyl alcohol (meth) acrylic acid derivative having the following general formula:

$$C_nF_{2n+1}(CH_2CF_2)_a(CF_2CF_2)_b(CH_2CH_2)_cOCOCR'\!=\!CH_2 \quad [Ib]$$

(wherein R' is a hydrogen atom, or a methyl group ; n is an integer of 1 to 6 ; a an integer of 1 to 4 ; b an integer of 1 to 3 ; and c and integer of 1 to 3, the adjacent group to the $C_nF_{2n+1}$ group having an $CH_2CF_2$ group), which process comprises subjecting a polyfluoroalkyl alcohol represented by the following general formula:

$$C_nF_{2n+1}(CH_2CF_2)_a(CF_2CF_2)_b(CH_2CH_2)_cOH \quad [Ia]$$

(where n, a, b, and c have the same meanings as defined above) to esterfication with acrylic acid or methacrylic acid.

* * * * *